United States Patent [19]

Kompis et al.

[11] Patent Number: 4,720,546

[45] Date of Patent: Jan. 19, 1988

[54] INTERMEDIATES FOR THE PREPARATION OF SUBSTITUTED 2-PHENYL-1,3-DIOXOLANES

[75] Inventors: Ivan Kompis, Oberwil, Switzerland; Ekkehard Weiss, Inzlingen, Fed. Rep. of Germany

[73] Assignee: Hoffman-La Roche Inc., Nutley, N.J.

[21] Appl. No.: 926,944

[22] Filed: Nov. 4, 1986

Related U.S. Application Data

[62] Division of Ser. No. 764,370, Aug. 12, 1985, Pat. No. 4,640,918.

[30] Foreign Application Priority Data

Aug. 31, 1984 [CH] Switzerland ................. 4177/84

[51] Int. Cl.[4] ................. C07D 279/12; C07D 417/12
[52] U.S. Cl. ................... 544/58.2; 544/59; 544/60
[58] Field of Search ................. 544/58.2, 59, 60

[56] References Cited

FOREIGN PATENT DOCUMENTS 2602770 7/1976 Fed. Rep. of Germany .
2804096 8/1978 Fed. Rep. of Germany .

OTHER PUBLICATIONS

Foster et al., Chemical Abstracts, vol. 83 (1975), 22183c.
J. Heeres et al., J. Med. Chem. 22, 1003 (1979).
J. Heeres et al., J. Med. Chem. 26, 511 (1983).

Primary Examiner—Richard L. Raymond
Attorney, Agent, or Firm—Jon S. Saxe; Bernard S. Leon; William G. Isgro

[57] ABSTRACT

The compounds of the formula

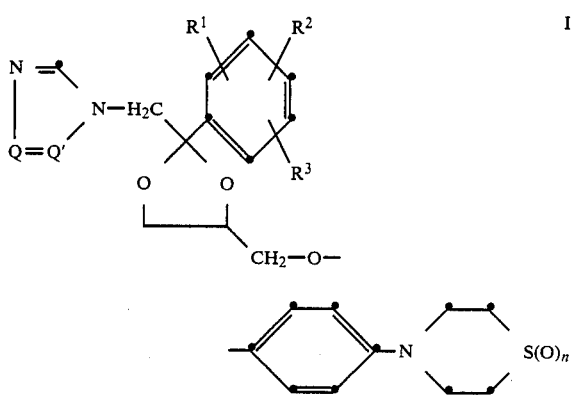

wherein one of the symbols Q and Q' is the group —CH= and the other is the group —CH= or —N=, $R^1$, $R^2$ and $R^3$ each independently are hydrogen or halogen and n is the integer 0, 1 or 2, and their pharmaceutically acceptable acid addition salts, which have valuable antimycotic properties and can be used for the control of infections caused by pathogenic fungi, are described.

3 Claims, No Drawings

INTERMEDIATES FOR THE PREPARATION OF SUBSTITUTED 2-PHENYL-1,3-DIOXOLANES

This is a division of application Ser. No. 764,370 filed Aug. 12, 1985, now U.S. Pat. No. 4,640,918.

BRIEF SUMMARY OF THE INVENTION

The invention relates to 2-phenyl-1,3-dioxolanes of the formula

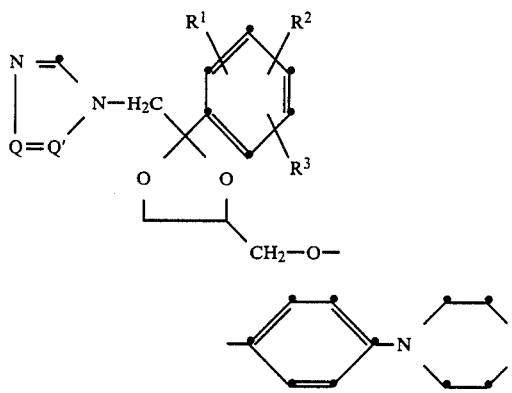

wherein one of the symbols Q and Q' is the group —CH= and the other is the group —CH= or —N=, $R^1$, $R^2$ and $R^3$ each independently is hydrogen or halogen and n is the integer 0, 1 or 2, and pharmaceutically acceptable acid addition salts thereof. The compounds of formula I possess valuable antimycotic properties and are therefore useful for the control of infections which are caused by pathogenic fungi.

DETAILED DESCRIPTION OF THE INVENTION

The invention relates to 2-phenyl-1,3-dioxolanes of the formula

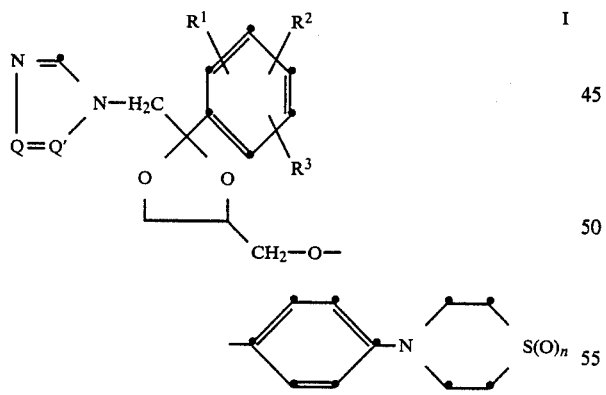

wherein one of the symbols Q and Q' is the group —CH= and the other is the group —CH= or —N-, $R^1$, $R^2$ and $R^3$ each independently is hydrogen or halogen and n is the integer 0, 1 or 2, and pharmaceutically acceptable acid addition salts thereof. The compounds of formula I possess valuable antimycotic properties and can be used for the control of infections which are caused by pathogenic fungi.

The invention comprises the compounds of formula I and their pharmaceutically acceptable acid addition salts, processes and intermediates for their preparation, medicaments containing them and their preparation, as well as their use in the control of prevention of illnesses and for the preparation of antimycotically active medicaments.

As used herein, the term "halogen" denotes chlorine, bromine, fluorine and iodine. The term "leaving group" denotes atoms or groups which are readily exchangeable by substitution, for example, halogen atoms, such as, chlorine, bromine and iodine; lower alkyl-sulfonyloxy groups, such as methanesulfonyloxy and arylsulfonyloxy, such as, the p-toluene-sulfonyloxy group. In this connection, preferred aryl groups are phenyl groups optionally substituted by lower alkyl or halogen. The term "lower alkyl" denotes straight-chain or branched saturated hydrocarbon residues with up to 7, preferably up to 4, carbon atoms, such as, methyl, ethyl, propyl, butyl, isobutyl, pentyl, heptyl and the like.

In a preferred embodiment, Q and Q' both are the group —CH=. Preferably, $R^1$ and $R^2$ are halogen and $R^3$ is hydrogen. In a particularly preferred embodiment, $R^1$ and $R^2$ are chlorine and $R^3$ is hydrogen, and $R^1$ and $R^2$ are situated in the 2- and 4-position, respectively. Preferably, n is 2.

An especially preferred compound of formula I is:

cis-4-[4-[[2-(2,4-Dichlorophenyl)-2-[(imidazol-1-yl)methyl]-1,3-dioxolan-4-yl]methoxy]phenyl]-tetrahydro-4H-1,4-thiazine 1,1-dioxide.

Other representative examles of the compounds of formula I are:

cis-4-[4-[[2-(2,4-Dichlorophenyl)-2-[(imidazol-1-yl)methyl]-1,3-dioxolan-4-yl]methoxy]phenyl]-tetrahydro-4H-1,4-thiazine;

cis-4-[4-[[2-(2,4-dichlorophenyl)-2-[(imidazol-1-yl)methyl]-1,3-dioxolan-4-yl]methoxy]phenyl]-tetrahydro-4H-1,4-thiazine 1-oxide;

cis-4-[4-[[2-(2,4-dichlorophenyl)-2-[(1H-1,2,4-triazol-1-yl)methyl]-1,3-dioxolan-4-yl]methoxy]phenyl]tetrahydro-4H-1,4-thiazine;

cis-4-[4-[[2-(2,4-dichlorophenyl)-2-[(1H-1,2,4-triazol-1-yl)methyl]-1,3-dioxolan-4-yl]methoxy]phenyl]-tetrahydro-4H-1,4-thiazine 1-oxide;

cis-4-[4-[[2-(2,4-dichlorophenyl)-2-[(1H-1,2,4-triazol-1-yl]-1,3-dioxolan-4-yl]methoxy]phenyl]-tetrahydro-4H-1,4-thiazine 1,1-dioxide; and cis-4-[4-[[2-(2,4-dichlorophenyl)-2-[(4H-1,2,4-triazol-4-yl)methyl]-1,3-dioxolan-4-yl]methoxy]phenyl]-tetrahydro-4H-1,4-thiazine 1,1-dioxide.

The compounds of formula I and their pharmaceutically acceptable acid addition salts can be prepared by
(a) reacting a compound of the formula

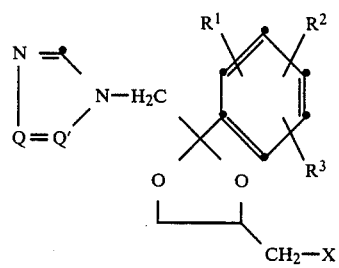

wherein Q, Q', $R^1$, $R^2$ and $R^3$ are as previously described and X is a leaving group, in the presence of a base with a compound of the formula

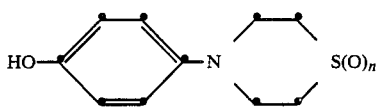

wherein n is as previously described, or
(b) converting a compound of the formula

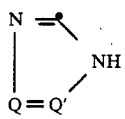

wherein Q and Q' are as previously described, or
(d) oxidizing a compound of the formula

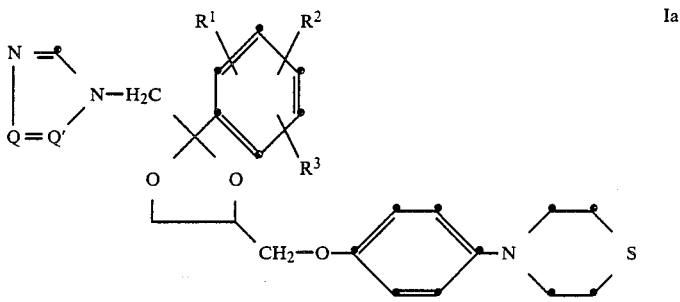

wherein $R^1$, $R^2$, $R^3$, Q and Q' are as previously described, at the sulfur atom, and (e) if desired, converting a compound of formula I into a pharmaceutically acceptable acid addition salt.

The reaction of a compound of formula II with a phenol of formula III in accordance with process variant (a) is preferably carried out in N,N-dimethylformamide, dimethyl sulfoxide or in an inert ether, such as, tetrahydrofuran, ethylene glycol dimethyl ether and t-butyl methyl ether. The leaving group denoted by X is preferably a lower alkylsulfonyloxy group or an arylsulfonyloxy group. The methanesulfonyloxy group is a particularly preferred leaving group. Suitable bases are, for example, sodium hydride, alkali metal hydroxides, such as, sodium hydroxide and potassium hydroxide and alkali metal carbonates, such as, potassium carbonate. In an especially preferred embodiment, there is used as the base sodium hydride which is dispersed in mineral oil. The reaction can be carried out in a temperature range of about 20° C. to about 100° C.

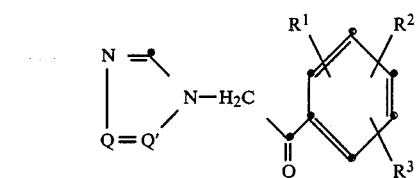

wherein Q, Q', $R^1$, $R^2$ and $R^3$ are as previously described, into the corresponding ketal with a glycol of the formula

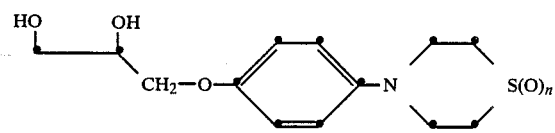

wherein n is as previously described, or
(c) reacting a compound of the formula

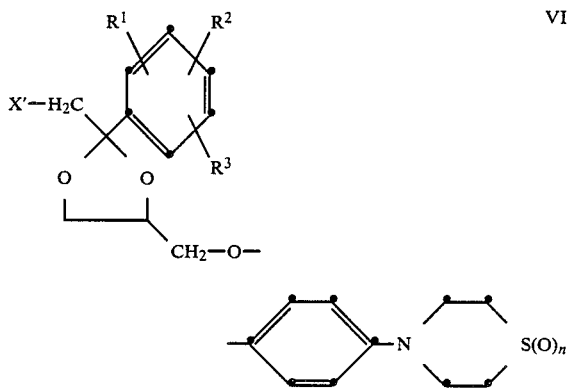

wherein $R^1$, $R^2$, $R^3$ and n are as previously described and X' is a leaving group, with a compound of the formula The reaction of a ketone of formula IV with a glycol of formula V to give the corresponding ketal in accordance with process variant (b) is preferably carried out in the presence of a strong acid, such as, p-toluenesulfonic acid and with azeotropic removal of the reaction water which is formed. Suitable solvents are, for example, aromatic hydrocarbons, such as, benzene, toluene and xylene, halogenated hydrocarbons, such as, methylene chloride and chloroform, as well as mixtures of these solvents with lower alcohols, such as, ethanol, propanol, butanol or pentanol. The reaction is carried out at the boiling temperature of the chosen solvent or at the boiling temperature of the chosen solvent mixture.

The reaction of a compound of formula VI with a compound of formula VII in accordance with process variant (c) is preferably carried out in an inert organic solvent, such as N,N-dimethylformamide, dimethylsulfoxide or N,N-dimethylacetamide in the presence of a base. Suitable bases are, for example, alkali metal carbonates, such as, sodium carbonate and potassium carbonate, alkali metal alcoholates, such as, sodium methanolate and potassium methanolate, tertiary amines, such as, triethylamine, sodium hydride and the like. As the base there can, however also be used the compound of formula VII which then, of course, must be used in excess. The leaving group denoted by X' is preferably a halogen atom, for example a chlorine, bromine or iodine atom. The reaction is conveniently carried out in a temperature range of about 0° C. to about 170° C.

The oxidation of a compound of formula Ia to give a compound of formula I in which n is the integer 1 in accordance with process variant (d) is preferably carried out with a peracid, such as, m-chloroperbenzoic acid in an inert organic solvent. Suitable solvents are, for example, halogenated hydrocarbons, such as, dichloromethane and chloroform. The reaction is preferably carried out in a temperature range of about −20° C. to room temperature.

The compounds of formula I can be converted into pharmaceutically acceptable acid addition salts. The preparation of such acid addition salts is carried out according to known methods and which are familiar to any person skilled in the art. There come into consideration not only salts with pharmaceutically acceptable inorganic acids, but also salts with pharmaceutically acceptable organic acids, for example hydrochlorides, hydrobromides, sulfates, nitrates, citrates, acetates, succinates, methanesulfonates, p-toluenesulfonates and the like.

The compounds of formula II in which Q is the group —N= and Q' is the group —CH= used as starting materials also form part of the invention and can be prepared by replacing the hydroxyl group in a compound of the formula

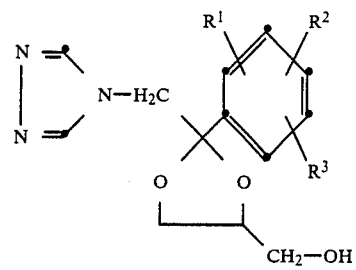

wherein $R^1$, $R^2$ and $R^3$ are as previously described, by a leaving group in a known manner or converting said hydroxyl group into a leaving group in a known manner. The lower alkylsulfonates and the arylsulfonates can be prepared, for example, by treating a compound of formula VIII with a corresponding sulfonic acid chloride in the presence of a base such as pyridine. The compounds of formula VIII and the remaining compounds of formula II are known substances.

The compounds of formula III in which n is the integer 2 used as starting materials also form part of the invention and can be prepared by reacting 4-aminophenol with divinyl sulfone in a lower alcohol, such as, ethanol. This reaction is preferably carried out in a temperature range of about room temperature up to the boiling point of the reaction mixture. The remaining compounds of formula III are known substances.

The compounds of formulas V and VI used as starting materials also form part of the invention and can be prepared, for example, in accordance with the following Reaction Scheme I.

Reaction Scheme I

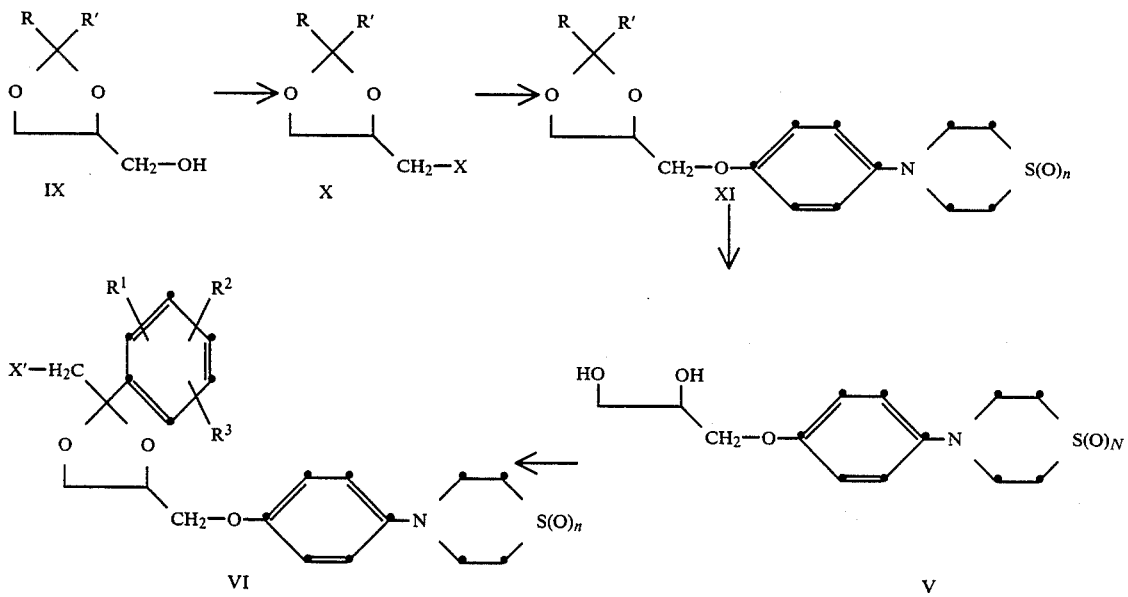

$R^1$, $R^2$, $R^3$, X, X' and n are as previously described; R and R' each independently is hydrogen or lower alkyl.

The compounds of formula X can be prepared from the known compounds of formula IX, an analogy to the preparation described above for the compounds of formula II, in which Q is the group —N= and Q' is the group —CH=, from compounds of formula VIII. The preparation of a compound of formula XI from a compound of formula X is carried out in analogy to the preparation of the compounds of formula I from compounds of formula II. The conversion of a compound of formula XI into a compound of formula V can be carried out, for example, by hydrolysis of the 1,3-dioxolane ring in the presence of water and a strong acid, such as, p-toluenesulfonic acid or by trans-acetalization in the presence of a lower alcohol, such as, methanol and an acid, such as, p-toluenesulfonic acid.

The preparation of the compounds of formula VI from compounds of formula V is carried out in analogy to the preparation of the compounds of formula I from the compounds of formula V, by reacting a compound of formula V with a compound of the formula

XII

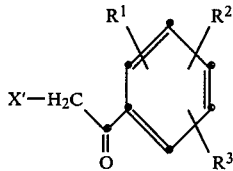

wherein $R^1$, $R^2$, $R^3$ and $X'$ are as previously described.

The compounds of formulas IX and XII used as starting materials are known substances.

The compounds of formula II in which Q is the group —N= and Q' is the group —CH=, the compounds of formula III in which n is the integer 2, as well as the compounds of formulas V and VI are also objects of the invention.

As already mentioned, the compounds of formula I and their pharmaceutically acceptable acid addition salts have valuable antimycotic properties. They are active against a large number of pathogenic fungi which cause topical and systemic infections. They are active, for example, against *Candida albicans* and *Histoplasma capsulatum*, which can be demonstrated, for example, as follows:

The test for checking for fungistatic activity is carried out in test tubes each of which contains 4.5 ml of Casiton agar and which have been sterilized at 120° C. for 15 minutes. The compounds to be investigated are dissolved in dimethyl sulfoxide in a concentration of 20 mg/ml, whereupon the solutions are diluted with sterile, distilled water to a concentration of 10 mg/ml. Subsequently, a series of solutions is prepared by diluting the original solution in succession in each case to a tenth of the original concentration by treatment with sterile, distilled water. To each test tube, which contains 4.5 ml of *Casiton agar*, there is then added in each case 0.5 ml of stock solution, whereby active substance concentrations of 100, 10, 1 or 0.1 µg/ml of medium are obtained.

Subsequently, cells of *Candida albicans*, cultures which are 24 hours old, are counted and $10^3$ cells per ml are placed in each of the previously prepared test tubes at 50° C., which are then placed on the slant. The cells of *Histoplasma capsulatum* are added to the test tubes in a concentration of about $10^7$ yeast cells per ml, there being used in this case cultures which are 3 days old. In the case of *Candida albicans* incubation is carried out for 48 hours at 37° C. and in the case of *Histoplasma capsulatum* incubation is carried out for 7 days at 30° C. The MIC values are thus determined after 48 hours or after 7 days. The thus-determined results are compiled in the following Table I. Moreover, this Table contains data concerning the acute toxicity of the compounds in accordance with the invention-$LD_{50}$ after single oral administration to mice:

TABLE I

| Q | Q' | n | $R^3$ | MIC values in µg/ml H. capsulatum | C. albicans | $LD_{50}$ in mg/kg |
|---|---|---|---|---|---|---|
| —CH= | —CH= | 0 | 2,4-Dichloro-phenyl | 10 | 1–100 | ca. 1000 |
| —CH= | —CH= | 1 | " | 10 | 1–100 | ca. 1000 |
| —CH= | —CH= | 2 | " | 1 | 0.1–1 | ≧4000 |
| —CH= | —N= | 0 | " | 10 | 0.1–1 | ≧5000 |
| —CH= | —N= | 1 | " | 100 | 1–100 | ca. 4000 |
| —CH= | —N= | 2 | " | 1 | 0.1–10 | ≧5000 |
| —N= | —CH= | 2 | " | >100 | 0.1–10 | ≧4000 |

The compounds of formula I in accordance with the invention can be used as medicaments in the form of pharmaceutical preparations. The pharmaceutical preparations can be administered enterally, for example, in the form of tablets, coated tablets, dragees, hard and soft gelatine capsules, solutions, emulsions, suspension or suppositories, parenterally, for example, in the form of injection solutions, or topically, for example, in the form of salves, creams or gels.

For the manufacture of such pharmaceutical preparations, the compounds of formula I in accordance with the invention can be processed with pharmaceutically inert, inorganic or organic carriers. Suitable carriers are, for example, lactose, maize starch or derivatives thereof, talc, stearic acid or its salts, vegetable oils, waxes, fats, semi-solid and liquid polyols, water, saccharose, invert sugar, glucose and the like.

Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically valuable substances. The manufacture of such pharmaceutical preparations is carried out according to known methods and which are familiar to any person skilled in the art.

As already mentioned, such pharmaceutical preparations and their manufacture also form part of the invention.

The products in accordance with the invention can be used in the control or prevention of illnesses, especially in the control of pathogenic fungi. The dosage can vary within wide limits and is, of course, fitted to the individual requirements of the host, i.e., warm-blooded animal, in each particular case. Depending on the mode of administration, substances in accordance with the invention are administered in a daily dosage of about 0.5 mg/kg to about 200 mg/kg.

The Examples which follow further illustrate the invention. However, they are in no way intended to limit the invention. All temperatures are given in degrees Celsius, unless otherwise stated.

EXAMPLE 1

(aa) A mixture of 99 g of hydroquinone, 13.5 g of copper(I) chloride and 180 ml of thiomorpholine is heated to boiling under reflux under argon for 47 hours. After cooling, the mixture is partitioned between 1N sodium hydroxide solution and dichloromethane, the sodium hydroxide extract is adjusted to about pH 1 with concentrated hydrochloric acid while cooling with ice and then partitioned between 0.1N hydrochloric acid and dichloromethane which contains 10% alcohol. The acidic extracts are adjusted to about pH 6 with 50 percent sodium hydroxide solution while cooling with ice and thereafter extracted in each case three times with dichloromethane which contains 10% alcohol as well as dichloromethane which contains 20% alcohol. The material obtained is distilled in a bulb-tube at 180° and 0.01 Torr and then recrystallized from methanol/ether. p-(Tetra-hydro-4H-1,4-thiazin-4-yl)phenol of melting point 156°–158° is obtained.

(ab) 23 ml of thiomorpholine are slowly added dropwise at about 80° to 17.17 g of p-fluoronitrobenzene in such a manner that the internal temperature does not rise above 110°. The mixture is then stirred at 120° for an additional 1 hour, whereupon it is extracted three times with 1 l of dichloromethane each time and the organic phases are washed three times with 500 ml of water each time, dried over sodium sulfate and evaporated. By recrystallization of the crude product from dichloromethane/ether, there is obtained 4-(p-nitrophenyl)-tetrahydro-4H-1,4-thiazine of melting point 142°–144°.

A solution of 23.47 g of 4-(p-nitrophenyl)-tetrahydro-4H-1,4-thiazine in 1.5 l of dioxane is hydrogenated over Raney-nickel until the hydrogen uptake has finished. Thereafter, the catalyst is removed by filtration, washed well with dioxane and the filtrate is evaporated in vacuo. By recrystallization of the crude product from dichloromethane/ether, there is obtained 4-(p-aminophenyl)-tetrahydro-4H-1,4-thiazine of melting point 109°–111°.

2.34 g of 4-(p-aminophenyl)-tetrahydro-4H-1,4-thiazine are dissolved in 12 ml of 35 percent sulfuric acid, 12 g of ice are added thereto, a cold solution of 1.05 g of sodium nitrite in 12 ml of water is then slowly introduced under the surface and the mixture is stirred for 5 minutes at about 0°. Thereafter, there are added 60 mg of urea, a solution of 144 g of copper(II) nitrate trihydrate in 420 ml of water and finally while stirring vigorously 1.59 g of copper(I) oxide. The mixture is stirred for 5 minutes, adjusted to about pH 6 with sodium hydroxide solution and extracted three times with 600 ml of dichloromethane each time and once with 600 ml of dichloromethane/ethanol (4:1). The organic phases are washed twice with 300 ml of water each time, dried over sodium sulfate and evaporated. The crude product is chromatographed on 400 g of silica gel with dichloromethane which contains 5% acetone. The material obtained is recrystallized from dichloromethane/methanol/ether, whereby there is obtained p-(tetrahydro-4H-1,4-thiazin-4-yl)phenol of melting point 155°–157°.

(b) A solution of 2.69 g of p-(tetrahydro-4H-1,4-thiazin-4-yl)phenol in 54 ml of N,N-dimethylformamide is added dropwise under argon to a mixture of 815 mg of sodium hydride dispersion (55%) in oil and 27 ml of N,N-dimethylformamide, whereupon the mixture is stirred for 30 minutes at 40°. Thereafter, a solution of 5.09 g of cis-[2-[2,4-dichlorophenyl-2-[(1H-imidazol-1-yl)methyl]]-1,3-dioxolan-4-yl]methyl methanesulfonate in 102 ml of N,N-dimethylformamide is added dropwise at 20°. The mixture is stirred for 2.5 hours at 90°, 150 ml of water are added thereto while cooling with ice and the mixture is extracted three times with 300 ml of dichloromethane each time. The organic phases are washed twice with 150 ml of water each time, dried over sodium sulfate and evaporated in vacuo. The residue is recrystallized from dichloromethane/ether, and there is obtained cis-4-[4-[[2-(2,4-dichlorophenyl)-2-[(imidazol-1-yl)methyl]-1,3-dioxolan-4-yl]methoxy]-phenyl]tetrahydro-4H-1,4-thiazine of melting point 164°–166°.

EXAMPLE 2

1.56 g of cis-4-[4-[[2-(2,4-dichlorophenyl)-2-[(imidazol-1-yl)methyl]-1,3-dioxolan-4-yl]methoxy]-phenyl]-tetrahydro-4H-1,4-thiazine are dissolved in 30 ml of dichloromethane, 600 mg of potassium carbonate are added thereto, the mixture is cooled to 0°, 17.5 ml of a 4.2 percent solution of m-chloroperbenzoic acid in dichloromethane/ethyl acetate (1:1) are added thereto and the mixture is then stirred for an additional 30 minutes at 0°. After the addition of 75 ml of water and 300 mg of sodium sulfite, the mixture is extracted three times with 150 ml of dichloromethane each time. The organic phases are washed with 10% potassium bicarbonate solution and water, dried over sodium sulfate and evaporated in vacuo. The crude product obtained is chromatographed on 390 g of silica gel while eluting with dichloromethane which contains 5% methanol. By recrystallization from ethanol/ether, there is obtained cis-4-[4-[[2-(2,4-dichlorophenyl)-2-[(imidazol-1-yl)methyl]-1,3-dioxolan-4-yl]methoxy-phenyl]-tetrahydro-4H-1,4-thiazine 1-oxide of melting point 174°–175°.

EXAMPLE 3

(a) A suspension of 8.74 g of 4-aminophenyl in 190 ml of ethanol is added dropwise at 50° to 11.34 g of divinyl sulfone, whereupon rinsing is carried out with 50 ml of ethanol and then the mixture is heated to boiling under reflux under argon for 3 hours. After cooling, the mixture is treated with 480 ml of water and stirred for 1 hour at 0°. The precipitated crystals are removed by filtration under suction, washed with 20 percent ethanol and water and dried. By recrystallization from dichloromethane/methanol/ether there is obtained 4-(p-hydroxyphenyl)-tetrahydro-4H-1,4-thiazine 1,1-dioxide of melting point 153°–155°.

(b) A solution of 3.08 g of 4-(p-hydroxyphenyl)-tetrahydro-4H-1,4-thiazine 1,1-dioxide in 62 ml of N,N-dimethylformamide is added dropwise to a mixture of 920 mg of sodium hydride dispersion (55%) in oil and 26 ml of N,N-dimethylformamide, whereupon the mixture is stirred for 15 minutes at 40° under argon. Thereafter, a solution of 4.93 g of cis-[2-(2,4-dichlorophenyl)-2-[(1H-imidazol-1-yl)methyl]-1,3-dioxolan-4-yl]methyl methanesulfonate in 99 ml of N,N-dimethylformamide is added dropwise thereto at 20°, the mixture is stirred under argon for 2.5 hours at 90°, treated with 150 ml of water while cooling with ice and extracted three times with 300 ml of dichloromethane each time. The organic phases are washed twice with 150 ml of water each time, dried over sodium sulfate and evaporated. The crude product is crystallized from dichloromethane/ether and recrystallized from ethanol, and there is obtained cis-4-[4-[[2-(2,4-dichlorophenyl)-2-[(imidazol-1-yl)methyl]-1,3-dioxolan-4-yl]methoxy]phenyl]-tetrahydro-4H-1,4-thiazine 1,1-dioxide of melting point 170°-172°.

EXAMPLE 4

A solution of 3.37 g of p-(tetrahydro-4H-1,4-thiazin-4-yl)phenol in 68 ml of N,N-dimethylformamide is added dropwise to a mixture of 1.02 g of sodium hydride dispersion (55%) in oil and 34 ml of N,N-dimethylformamide, whereupon the mixture is stirred for 30 minutes at 40° under argon. Thereafter, a solution of 6.38 g of cis-[[2-(2,4-dichlorophenyl)-2-[(1H-1,2,4-triazol-1-yl)methyl]-1,3-dioxolan-4-yl]methyl]methanesulfonate in 128 ml of N,N-dimethylformamide is added dropwise thereto at 20°. The mixture is stirred under argon for 2.5 hours at 90°, treated with 200 ml of water while cooling with ice and extracted three times with 400 ml of dichloromethane each time and once with dichloromethane/ethanol (4:1). The organic phases are washed successively twice with 200 ml of water each time, dried over sodium sulfate and evaporated in vacuo. The crystalline crude product is recrystallized from dichloromethane/ether, and there is obtained colorless cis-4-[4-[[2-(2,4-dichlorophenyl)-2-[(1H-1,2,4-triazol-1-yl)methyl]-1,3-dioxolan-4-yl]methoxy]phenyl]-tetrahydro-4H-1,4-thiazine of melting point 119°-121°.

EXAMPLE 5

A solution of 1.63 g of 90 percent m-chloroperbenzoic acid in 80 ml of dichloromethane is slowly added dropwise and while stirring vigorously at 0° to a mixture of 3.41 g of cis-4-[4-[[2-(2,4-dichlorophenyl)-2-[(1H-1,2,4-triazol-1-yl)methyl]-1,3-dioxolan-4-yl]methoxy]phenyl]-tetrahydro-4H-1,4-thiazine, 1.47 g of potassium carbonate and 130 ml of dichloromethane. After an additional 30 minutes at 0°, there are added thereto 320 ml of water and 1.14 g of sodium sulfite, whereupon the mixture is extracted three times with 320 ml of dichloromethane each time. The organic phases are washed once with 160 ml of 10 percent potassium bicarbonate solution and twice with 160 ml of water each time, dried over magnesium sulfate and evaporated. The crude product obtained is chromatographed on 650 g of silica gel with dichloromethane which contains 2-5% methanol. By crystallization of the material obtained from dichloromethane/ether and recrystallization from ethanol/ether, there is obtained cis-4-[4-[[2-(2,4-dichlorophenyl)-2-[(1H-1,2,4-triazol-1-yl)methyl]-1,3-dioxolan-4-yl]methoxy]phenyl]-tetrahydro-4H-1,4-thiazine 1-oxide of melting point 125°-129°.

EXAMPLE 6

In analogy to Example 3(b), from 4-(p-hydroxyphenyl)-tetrahydro-4H-1,4-thiazine 1,1-dioxide and cis-[[2-(2,4-dichlorophenyl)-2-[(1H-1,2,4-triazol-1-yl)methyl]-1,3-dioxolan-4-yl]methanesulfonate, there is obtained cis-4-[4-[[2-(2,4-dichlorophenyl)-2-[(1H-1,2,4-triazol-1-yl)methyl]-1,3-dioxolan-4-yl]methoxy]phenyl]-tetrahydro-4H-1,4-thiazine 1,1-dioxide of melting point 142°-144°.

EXAMPLE 7

(a) 2.04 g of cis-[2-(2,4-dichlorophenyl)-2-[(4H-1,2,4-triazol-4-yl)methyl]-1,3-dioxolan]-4-methanol of melting point 181°-182° are dissolved in 10 ml of pyridine, 1.13 g of methanesulfonyl chloride are added dropwise thereto at 0°, the mixture is stirred for 15 minutes at 20° and for 2.5 hours at 30°, then treated at 0° with 100 ml of water and stirred for 45 minutes at 0°. The precipitated crystals are removed by filtration under suction, washed with water and dried in vacuo. By recrystallization from dichloro-methane/ether, there is obtained cis-[[2-(2,4-dichlorophenyl)-2-[(4H-1,2,4-triazol-4-yl)methyl]-1,3-dioxolan-4-yl]methyl]methanesulfonate of melting point 135°-137°.

(b) A solution of 1.41 g of 4-(p-hydroxyphenyl)-tetrahydro-4H-1,4-thiazine 1,1-dioxide in 28 ml of N,N-dimethylformamide is added dropwise at 20° to a mixture of 540 mg of sodium hydride dispersion (55%) in oil and 12 ml of N,N-dimethylformamide, whereupon the mixture is stirred under argon for 15 minutes at 40°. A solution of 2.25 g of cis-[[2-(2,4-dichlorophenyl)-2-[(4H-1,2,4-triazol-4-yl)-methyl]-1,3-dioxolan-4-yl]methyl]methanesulfonate in 45 ml of N,N-dimethylformamide is then added dropwise thereto at 20° and the mixture is stirred under argon for 2.5 hours at 90°. Thereafter, 75 ml of water are added dropwise while cooling with ice, whereupon the mixture is extracted three times with 150 ml of dichloromethane each time. The organic phases are washed twice with 75 ml of water each time, dried over sodium sulfate and evaporated in vacuo. The crude product obtained is chromatographed on 660 g of silica gel with dichloromethane which contains 2-4% methanol. By crystallization from dichloromethane/ether and recrystallization from ethanol/ether, there is obtained cis-4-[4-[[2-(2,4-dichlorophenyl)-2-[(4H-1,2,4-triazol-4--yl)methyl]-1,3-dioxolan--4-yl]methoxy]phenyl]-tetrahydro-4H-1,4-thiazine 1,1-dioxide of melting point 202°-206°.

EXAMPLE A

The compound cis-4-[4-[[2-(2,4-dichlorophenyl)-2-[(imidazol-1-yl)methyl]-1,3-dioxolan-4-yl]methoxy]phenyl]-tetrahydro-4H-1,4-thiazine 1,1-dioxide can be used as follows as the active substance for the preparation of tablets:

| Ingredients | mg/tablet |
|---|---|
| A compound of formula I | 200 |
| Lactose powdered | 100 |
| Polyvinylpyrrolidone | 15 |
| Sodium carboxymethylstarch | 10 |
| Talc | 3 |
| Magnesium stearate | 2 |
| Tablet weight | 330 |

The active substance and the powdered lactose are mixed intensively. The mixture obtained is then moistened with an aqueous solution of polyvinylpyrrolidone and kneaded, whereupon the mass obtained is granulated, dried and sieved. The granulate is mixed with the remaining ingredients and the mixture is then pressed into tablets of suitable size.

We claim:

1. A compound, 4-(p-Hydroxyphenyl)-tetrahydro-4H-1,4-thiazine 1,1-dioxide.
2. A compound of the formula
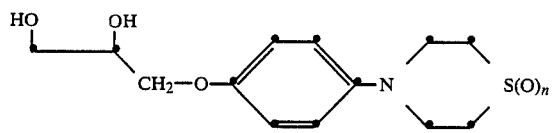
V
wherein n is the integer 0, 1 or 2.
3. A compound of the formula
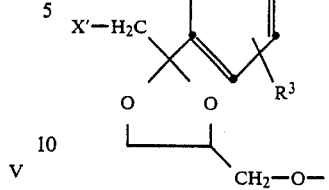
VI
wherein $R^1$, $R^2$ and $R^3$ each independently are hydrogen or halogen, X' is a leaving group and n is the integer 0, 1 or 2.
* * * * *